United States Patent [19]

Kiesele et al.

[11] Patent Number: 5,344,546

[45] Date of Patent: * Sep. 6, 1994

[54] ELECTRICAL MEASURING CELL FOR DETERMINGING AMMONIA, AMINES, HYDRAZINE AMINES, HYDRAZINE AND HYDRAZINE DERIVATIVES

[75] Inventors: Herbert Kiesele; Stephan Haupt, both of Lübeck; Uwe Kühn, Wesenberg, all of Fed. Rep. of Germany

[73] Assignee: Dragerwerk Aktiengesellschaft, Lübeck, Fed. Rep. of Germany

[*] Notice: The portion of the term of this patent subsequent to Jul. 20, 2010 has been disclaimed.

[21] Appl. No.: 19,764

[22] Filed: Feb. 19, 1993

Related U.S. Application Data

[63] Continuation-in-part of Ser. No. 804,722, Dec. 11, 1991, Pat. No. 5,228,974, which is a continuation-in-part of Ser. No. 507,755, Apr. 12, 1990, Pat. No. 5,076,904.

[30] Foreign Application Priority Data

Apr. 29, 1989 [DE] Fed. Rep. of Germany ....... 3914284
Feb. 20, 1992 [DE] Fed. Rep. of Germany ....... 4205157

[51] Int. Cl.$^5$ ............................................. G01N 27/404
[52] U.S. Cl. ................... 204/415; 204/153.14; 204/412
[58] Field of Search ............... 204/153.14, 153.17, 204/412, 415, 431, 432

[56] References Cited

U.S. PATENT DOCUMENTS

| | | | |
|---|---|---|---|
| 2,651,612 | 9/1953 | Haller | 204/431 |
| 2,898,282 | 8/1959 | Flook, Jr. et al. | 204/432 |
| 3,260,656 | 7/1966 | Ross, Jr. | 204/415 |
| 3,515,658 | 6/1970 | Amdur | 204/415 |
| 3,649,505 | 3/1972 | Strickler et al. | 204/415 |
| 3,719,576 | 3/1973 | Macur | 204/415 |
| 3,830,718 | 8/1974 | Riseman et al. | 204/415 |
| 3,849,201 | 11/1974 | Kordesch | 429/9 |
| 3,966,579 | 6/1976 | Chang et al. | 204/415 |
| 4,051,006 | 9/1977 | Neti et al. | 204/415 |
| 4,127,462 | 11/1978 | Blurton et al. | 204/432 |
| 4,169,779 | 10/1979 | Tataria et al. | 204/415 |
| 4,201,634 | 5/1980 | Stetter | 204/432 |
| 4,599,157 | 7/1986 | Suzuki et al. | 204/432 |
| 4,900,405 | 2/1990 | Otagawa et al. | 204/412 |
| 4,940,525 | 7/1990 | Enzell et al. | 204/296 |
| 5,076,904 | 12/1991 | Kiesele et al. | 204/153.14 |

OTHER PUBLICATIONS

"Reference Electrodes, Theory and Practice" by D. Ives et al., Academic Press, New York, 1961, pp. 356 to 360.

"Encyclopedia of Electrochemistry of the Elements", vol. 8, 1978, p. 413.

"CRC Handbook of Chemistry and Physics", 69th Edition, 1988 to 1989, p. E42.

*Primary Examiner*—T. Tung
*Attorney, Agent, or Firm*—Walter Ottesen

[57] ABSTRACT

The invention is directed to an electrochemical cell for measuring ammonia, amines, hydrazine and hydrazine derivatives and includes a measuring electrode in an electrolyte. The measuring electrode is provided with a coating made of a transition metal oxide and is improved in that its measuring sensitivity during long-term loading is increased. The cross sensitivity of the measuring cell is reduced especially with respect to $NO_2$ and $SO_2$. For this purpose, the oxide constituents of the coating are made of a metal conducting oxide of one element or an oxide mixture of several elements of the platinum metal group. Oxides of ruthenium and iridium have proven especially useful. The invention is also directed to an electrochemical measuring cell for measuring ammonia or hydrazine and includes at least a measuring electrode and a counter electrode in an electrolyte. The measuring cell provides a signal increase having a shorter response time and an improved signal stability. For this purpose, the electrolyte is an aqueous solution of a hygroscopic salt of an alkali metal or alkaline earth metal such as calcium nitrate or lithium nitrate or a mixture of both salts.

21 Claims, 2 Drawing Sheets

ELECTRICAL MEASURING CELL FOR DETERMINGING AMMONIA, AMINES, HYDRAZINE AMINES, HYDRAZINE AND HYDRAZINE DERIVATIVES

RELATED APPLICATIONS

This is a continuation-in-part of application Ser. No. 07/804,722, filed Dec. 11, 1991, and entitled "Electrochemical Measuring Cell for Determining Ammonia or Hydrazine in a Measuring Sample", now U.S. Pat. No. 5,228,974, which, in turn, is a continuation-in-part of application Ser. No. 07/507,755, filed Apr. 12, 1990, and entitled "Electrochemical Measuring Cell for Determining Ammonia or Hydrazine in a Measuring Sample", now U.S. Pat. No. 5,076,904.

FIELD OF THE INVENTION

The invention relates to an electrochemical measuring cell for determining ammonia, amines, hydrazine and hydrazine derivatives in a fluid (gaseous or liquid) measuring sample. The measuring cell has at least one measuring electrode and at least one counter electrode of which at least the measuring electrode is provided with a coating containing a transition-metal oxide. The electrodes are arranged in an electrolyte chamber filled with a soluble electrolyte. The electrolyte chamber is closed off with respect to the measuring sample by a permeable membrane.

BACKGROUND OF THE INVENTION

An electrochemical measuring cell for measuring the ammonia content of a sample is disclosed in U.S. Pat. No. 3,649,505 and includes a pH-electrode as a measuring electrode which is used to measure hydrogen ions. This potentiometric measurement of an ammonia concentration requires a long time duration for a completed measuring reaction. The long time duration is needed for the adjustment of an equilibrium. In this time duration, the $NH_3$ to be detected and the water content of the electrolyte conjointly form $NH_4OH$ which, in turn, dissociates into $NH_4^+$ ions and $OH^-$ ions. The slow step determining the speed for this reaction is the adjustment of the equilibrium with the gas space or the adjustment of the equilibrium at the glass membrane.

The glass electrode required for the pH-measurement changes in the characteristic of the glass membrane in the course of its use so that drift phenomena occur. A stable reference potential is necessary for carrying out the pH-measurement and a displacement of this reference potential in the course of use likewise leads to drift phenomena. The known measuring cell responds to all gases influencing the pH-value of the electrolyte so that its selectivity for measurements in corresponding gas mixtures is not adequate.

Ammonia is an important base chemical in the chemical industry (for example fertilizers) and is utilized in increasing quantities in cooling and $NO_x$-removal facilities (power plants). Furthermore, ammonia is generated in large quantities where vast numbers of animals are held. The concentration of ammonia must be monitored to preclude a dangerous situation.

Amines are important synthesizing components in the chemical industry and are generated by natural breakdown processes (food industry). Hydrazine and hydrazine derivatives play an important role in three areas, namely, in the chemical industry, in the protection against corrosion (boiler water) and in the area of rocket fuels. In all cases, a continuous and sensitive measurement is necessary in order to monitor appropriate facilities and, if necessary, provide a warning against dangerous concentrations.

SUMMARY OF THE INVENTION

It is an object of the invention to provide an electrochemical measuring cell of the kind described above which is improved so that a selective ammonia measurement is obtained providing the following: short response time, a linear response and a low tendency to drift. It is a further object of the invention to provide such an electrochemical measuring cell having electrodes which are so configured that the oxidation of the ammonia or hydrazine as a measurement reaction has no influence on the sensitivity of this measuring cell.

The electrochemical measuring cell of the invention is for determining ammonia or hydrazine in a fluid measuring sample. The measuring cell includes: a housing having an opening directed toward the sample to be measured and defining an electrolyte chamber; a soluble electrolyte contained in the chamber; a permeable membrane mounted on the housing for closing off the chamber; a measuring electrode and a counter electrode disposed in the chamber so as to be in spaced relationship to each other; and, the measuring electrode having a coating containing cobalt oxide and the coating being formed on the measuring electrode so as to be in direct contact with the electrolyte.

The advantage of the invention is essentially that the oxidation of the ammonia at the measuring electrode is catalyzed by the cobalt oxide coating so that no disturbing secondary products develop at the measuring electrode which could hinder an oxidation which follows. Furthermore, no blocking of the electrode occurs because of an electrochemically inert passive layer.

The measuring cell according to the invention affords the advantage that it offers a very good long-term stability and negligible drift. Also, very high concentrations of ammonia can be measured because of the catalytically effective oxide layer. These high concentrations are rendered harmless with respect to catalytic poisons or disadvantageous influences of the electrolyte for the operational capability of the measuring cell. Because of the coating of cobalt oxide, the oxidation of ammonia at the measuring electrode surface occurs so rapidly that the ammonia concentration at this electrode surface is practically zero. This results in a high concentration gradient between the measuring sample and the surface of the measuring electrode. In this way, the measuring cell reaction is returned to a transport-controlled reaction without restrictive reaction steps. This leads to a rapid response time and to a high sensitivity of the measuring cell. Gold, platinum or iridium can be selected as a carrier material for the electrode. The measuring cell of the invention is equally well suited for detecting hydrazine.

For producing a cobalt oxide coating, a carrier material of gold defining the electrode can, for example, be dipped into a cobalt nitrate solution or a cobalt acetate solution and cobalt oxide is then electrically deposited thereon. Potassium nitrate can be added to the cobalt solution as a conductive electrolyte. Another method for forming the cobalt oxide coating is to form the carrier material for the electrode from a cobalt-containing alloy which is then oxidized.

Carrier materials for electrochemically measuring ammonia can be used by applying the coating containing cobalt oxide. Without this coating, a surface passivation in the form of a nitride formation occurs whereby the measuring sensitivity is reduced to the point that the measuring cell is unusable. In this connection, reference may be made to the "Encyclopedia of Electrochemistry of the Elements", Volume 8, 1978, page 413.

With respect to the measuring cell of the invention, it is emphasized that there is no cross-sensitivity against carbon monoxide or hydrogen.

In order to generate a reference potential for determining ammonia or hydrazine, a reference electrode is introduced into the measuring cell having a potential which functions as a reference point for the measurement. It is advantageous to likewise provide such a reference electrode with a coating containing cobalt oxide. A measuring cell of this kind affords the advantage that it can be stored with short-circuited electrodes whereby it is immediately operationally ready because of the short warm-up time. Furthermore, the dependency of the residual current on temperature is minimized since the potential of the measuring electrode and of the reference electrode are influenced in the same manner by the temperature.

U.S. Pat. No. 5,076,904 discloses a measuring cell wherein the $NH_3$ molecules diffuse from the gas phase through the porous membrane and a thin electrolyte film to the electrode where they are anodically oxidized. The permeability of the gas to be measured in the electrolyte film is essential for a high sensitivity of the sensor. The minimum operating temperature of the sensor is limited by the freezing point of the electrolyte while the service life of the sensor is determined primarily by the water vapor pressure of the electrolyte.

Accordingly, it is still another object of the invention to improve a measuring cell of the kind described in the above-mentioned U.S. Pat. No. 5,076,904 to increase the sensitivity as well as to lower the operating temperature and increase the service life.

The above object is achieved by providing as an electrolyte, an aqueous solution of a hygroscopic salt of an alkali metal or an alkaline earth metal or a mixture of both salts.

The hygroscopic salts effect a reduction of the freezing point so that the sensors can be utilized down to a temperature of $-50°$ C. in refrigerating plants or in open air. The water vapor pressure of the electrolyte solution is reduced so that the liquid loss is slowed and a large electrolyte reservoir is unnecessary.

If, as an example, a hygroscopic salt such as lithium nitrate, magnesium nitrate or calcium nitrate or a mixture of these salts is selected, then ammonia and hydrazine form complexes or complex-type bonds with the cations. In this way, the solubility and the permeability and therefore the sensitivity is increased.

For the invention, the salt added must be hygroscopic in order to bind water vapor from the atmosphere and thereby prevent the electrolyte from drying up. A reduction in freezing point takes place according to chemical laws with a high addition of salt in a solution. The reduction of the freezing point is associated with a reduction in vapor pressure.

To further improve the electrochemical measuring cell, it is advantageous to provide the measuring electrode with a coating containing cobalt oxide with the coating being so applied on the measuring electrode that the electrode is in direct contact with the electrolyte. An improved protection of the measuring electrode surface against disturbing reactions of reaction products is obtained with the cobalt oxide coating.

If a so-called three-electrode measuring cell is utilized, then it is advantageous to provide a reference electrode in the electrolyte which likewise has a coating containing cobalt oxide.

The measuring electrode and reference electrode can preferably be made of a precious metal such as gold with the coating being deposited electrolytically on the carrier material of the electrode.

It can be just as advantageous to produce the measuring electrode and the reference electrode from a carrier which comprises a cobalt alloy and with the coating being formed from an oxide layer which is obtained by oxidation of the alloy.

For an electrode material having a cobalt oxide coating, it is advantageous to add a soluble cobalt salt to the electrolyte. The cobalt salt acts as a catalyzer in that it regenerates the cobalt oxide coating if the coating should become damaged during operation of the measuring cell. Furthermore, the cobalt salt supports the catalytic reaction of the ammonia oxidation or hydrazine oxidation at the measuring electrode in the electrolyte. In this way, the sensitivity and the response speed of the chemical measuring cell are increased.

An advantageous cobalt salt for this purpose is cobalt nitrate. By using the cobalt salt and especially cobalt nitrate, the generation of a new cobalt oxide layer is favored insofar as it is attacked by a chemical disturbance reaction. An especially suitable mixture for the electrolyte is a 3.5 molar solution of calcium nitrate or lithium nitrate and a 0.1 millimolar cobalt nitrate admixture as a catalyzer. The admixture of cobalt nitrate can be increased up to 1 millimol without the detection function of the measuring cell being affected.

It is emphasized that the electrochemical measuring cell of the invention has no cross sensitivity with respect to carbon monoxide and hydrogen.

A reference electrode is introduced into the measuring cell to generate a reference potential for the determination of ammonia or hydrazine. The potential of the reference electrode defines a reference point for the measurement. It is advantageous to likewise provide such a reference electrode with a coating containing cobalt oxide.

A measuring cell of this kind affords the advantage that the cell can be stored with its electrodes short circuited whereby the cell is immediately operationally ready because of the short run-in time. Furthermore, the dependence of the base current on the temperature is minimized since the potential of the measuring electrode and the reference electrode is influenced in the same manner by the temperature.

U.S. Pat. No. 3,830,718 is now referred to because a potentiometric ammonia sensor is disclosed therein. This ammonia sensor exploits the change of the pH value and utilizes an acidic electrolyte, namely, ammonium picrate (a saturated solution containing only 0.05 M picrate). The ammonium salt is added in order to have a concentration as constant as possible of ammonium ions in the solution because this concentration is destroyed with the presence of ammonia. This disturbance is applied for making ammonia measurements.

The addition of NaCl of KCl is necessary in order to maintain a standard chlorine concentration for the Ag-/AgCl reference electrode. The concentration amounts to only 0.0001 to 0.1 Mol/liter as noted in this patent.

Table I lists the above chloride salts as well as the chloride salt $NH_4Cl$ presented in U.S. Pat. No. 3,830,718 and shows the complete solidification of the electrolyte solutions at low temperatures. The concentrations of these salts listed in the table correspond to those given in the patent. The solutions of these salts were cooled down in a climatic chamber and the temperatures shown in Table I indicate the complete solidification of the electrolyte already at $-5°$ C.

Table II lists test results for salts for the ammonia and hydrazine sensor according to the invention. As shown in this table, $LiNO_3$ at 3.5 Mol/liter is acceptable and provides for gas and ion transport to just above $-20°$ C.

Chloride and bromide salts are suitable for electrochemical measuring cells wherein at least the measuring electrode has a coating having oxide constituents selected from a metal conductive oxide of at least one element of the platinum metal group or a metal conductive oxide mixture of several elements of the platinum metal group. On the other hand, nitrate salts are suitable for electrochemical measuring cells having a measuring electrode having a coating containing cobalt oxide as already described herein.

The calcium nitrate $Ca(NO_3)_2$ is listed in Table II for the purposes of comparison and has been successfully utilized.

The measuring cells described above include at least one measuring electrode and one counter electrode in an electrolytic chamber and, if necessary, also a reference electrode. At least the measuring electrode is provided with a coating of cobalt oxide. This oxide electrode is in direct contact with the electrolyte. The ammonia or hydrazine (or derivatives of these compounds) to be detected are anodically oxidized directly at the surface of the oxide electrode. In this way, a short response time is obtained even at high concentrations of the toxic substance to be detected; however, it has been shown that for a constant high continuous loading over a longer time span of weeks and months, the measuring sensitivity deteriorates so greatly after too short a time that, for example, a recalibration is necessary. Furthermore, the measuring cell described above is to a large extent cross-sensitive with respect to $NO_2$ and $SO_2$. These two gases can occur in areas of use of the above-described measuring cell such as in power plants. For this reason, this cross-sensitivity is very disadvantageous for a measurement of a specific type of gas.

In view of the above, it is still another object of the invention to improve this measuring cell so that: its measuring sensitivity is increased, the signal stability for continuous loading is improved and its cross-sensitivity is reduced.

According to a feature of the invention, the oxide constituents of the coating are formed from a conductive metal oxide or oxide mixture of an element of the platinum metal group.

The advantage of this embodiment of the invention is essentially seen in that a measuring cell of this kind is characterized by a high long-term stability. No measurable signal drop was obtained, for example, for a continuous loading at 80 ppm ammonia over several weeks. The sensitivity of the measuring cell could be increased by a factor of two to three because of the larger ratio of signal current to base current. The absence of cross-sensitivity with respect to $NO_2$ and $SO_2$ as well as with respect to further substances such as $CH_4$, $CO$, $CO_2$ and chlorine make possible a clear measurement with respect to a specific type of gas. Furthermore, the dynamic range of measurement which is approximately ten times greater should also be emphasized. This dynamic measurement range was covered by the measuring cell even under continuous loading. A blocking of the electrode surface with respect to the electrochemical reaction taking place in the electrolyte is avoided (electrode poisoning) by the closed oxide layer on the measuring electrode.

The elements ruthenium, rhodium, osmium and iridium are metallic conductive oxides of the platinum metal group which are suitable. All these elements form a dioxide of tetragonal crystal structure which is characterized by a low specific resistance in the order of magnitude of $10^{-5}$ to $10^{-4}$ ohm$\times$cm.

The metals ruthenium and iridium have proven especially desirable because of their reproducible and definable characteristics for the production of electrodes as well as the oxide coating. An especially good electrode configuration comprises an electrode carrier made of iridium coated with an oxide layer of iridium oxide. The formation of the measuring electrode takes place best in that it is configured in the manner of a gas diffusion electrode wherein a PTFE-membrane is coated with a base material of iridium to which the iridium oxide layer is applied. The coating can be carried out very simply with the aid of a thermal process (decomposition of metal salts) or the coating can be applied to the base material in a sputtering process. A suitable cover coating is formed also when anodically loading iridium electrodes in the event that the electrode potential is 400 mV or more. The reference electrode is then an iridium sinter electrode. The formation of the oxide coating takes place by means of electrochemical oxidation of the iridium in the measuring cell itself. Coatings produced in this manner are characterized by a dense structure of adequate thickness.

The quality of the oxide coating is improved with the aid of a mixture of oxides of several elements of the platinum metal group. Accordingly, the resistance to corrosion of the oxide layer is increased, for example, by the addition of iridium oxide to ruthenium oxide. Here, it is advantageous to configure the base body out of that metal which is present as a primary component in the metal oxide or oxide mixture. In this way, a good stability is provided especially for the production of a diffusion electrode.

A further oxide of the group of transition metals can be admixed to the metal oxide or oxide mixture. For example, the overvoltage for the generation of oxygen is increased by an admixture of $SnO_2$ and therefore the base current is reduced.

The use of the measuring cell in power plants makes it desirable to prevent, especially during long-term measurement and/or monitoring, an exsiccation of the electrolyte. It is necessary to make measurements at low temperature for use in refrigeration facilities. For this purpose, a hygroscopic alkali salt or alkaline earth salt is selected as the supporting electrolyte. This supporting electrolyte provides a neutral to slightly acidic pH-value when dissolved in water. Such an electrolyte is characterized by a low water-vapor pressure as well as a low freezing point which permits a minimum operating temperature for the measuring cell down to $-50°$ C. It is also an advantage that the surface tension is much greater than with alkaline solutions as this results in a housing having an increased seal tightness thereby preventing liquid from entering fissures in the cell. Still another advantage is that the generation of carbonate with $CO_2$ in the ambient air is prevented which would otherwise cause the solution to deteriorate.

Lithium nitrate ($LiNO_3$), calcium nitrate ($CaNO_3)_2$ as well as lithium chloride (LiCl) and calcium chloride (CaCl) are examples of such alkali or alkaline earth salts in a concentration of approximately 3.5 to 6 molar and which can be increased up to 10 molar. The most advantageous characteristics are obtained for a 6 molar solution to which ammonium salts (for example $NH_4NO_3$ or $NH_4Cl$) in concentrations of $10^{-3}$ to $10^{-1}$ M are added for additional stabilization of the pH-value in electrolytes.

Ammonium ions are made available to the electrolyte by means of the ammonium salts thereby preconditioning the measuring cell. Protons are released during the anodic oxidation of $NH_3$ and these protons combine with the $NH_3$ which follows to form ammonium ions. If an ammonium salt is added ab initio to the electrolyte then the relative change of the $NH_4^+$ concentration is less and the pH-value is stabilized. A sensor preconditioned in this manner supplies a more stable signal.

If LiCl is selected as the supporting electrolyte, then, in addition to the freezing point being reduced, the solubility of $NH_3$ is expanded by means of a complex formation. In the solution, the lithium ions are surrounded by a solrate sheath of $H_2O$ molecules which are displaced by the $NH_3$ molecules when these molecules penetrate from the ambient into the electrolyte via diffusion. In this way, an "$NH_3$-packet" is formed as a sheath of the Li atom and reaches the measuring electrode whereby the detection sensitivity of the measuring cell is increased.

The pH-value of the electrolyte solution is changed in the vicinity of the operating electrode as well as the auxiliary electrode when the measuring sample enters the electrolyte. For example, this is explained in the following table for the case of exposure to ammonia:

| Working electrode: | $2 NH_3 = N_2 + H^+ 6 e^-$ |
| --- | --- |
| | $6 NH_3 + 6 H^{8+} = 6 NH_4^+$ |
| | $8 NH_3 = N_2 + 6 NH_4^+ + 6 e^-$ |
| Counter electrode: | $O_2 + 2 H_2O + 4 e^- = 4 OH^-$ |
| Working potential: | $\geq 400$ mV |

The formed hydroxide ions ($OH^-$) reach the working and reference electrodes via diffusion after several hours. By shaking the sensor, the convection leads to a thorough mixing of the electrolyte solution within seconds. This leads to a potential shift of the reference electrode and to a pH-change of the working electrode and therefore to a signal drift. To prevent this, it is advantageous to build in an ion exchange membrane between the measuring electrode and the counter electrode to prevent the hydroxide ion transport. In this way, disturbing ions are trapped at the membrane and do not reach the measuring electrode. An ion exchange membrane made of Nafion (perfluorosulfonated PTFE) has been shown to be especially advantageous. This membrane can either be clamped within the electrolyte chamber in the housing of the measuring cell as an independent membrane or this membrane can directly cover the surface of the working electrode.

A thorough mixing of the electrolyte, that is, a convection of the hydroxide ions which is too rapid, can be prevented within wide limits in that the electrolyte is saturated in a tightly packed wick made of glass wool which, in turn, is brought into contact with the electrodes (electrolyte wick).

It is advantageous to form the counter electrode from the same composition as the measuring electrode in order to further increase the measuring stability of the measuring cell.

The counter electrode is comprised of a porous base body (membrane) which is provided with a porous oxide coating of an element on the side facing the electrolyte or an oxide mixture of several elements of the platinum metal group. The surface of the porous counter electrode not provided with the coating is disposed within the measuring cell housing but outside of the inner space filled with the electrolyte. This surface is covered with a filter which can bind ammonia. The filter serves to take up ammonia formed from the ammonium ions by the electrochemical reaction at the counter electrode because, otherwise, the ammonia would diffuse back to the measuring electrode or to the reference electrode and would there contribute to a falsification of the measuring value. Activated charcoal can be used as a filter material which is charged either with $ZnSO_4$ or phosphoric acid. The total volume of the filter material is 3 mL. This quantity makes possible a continuous operation of more than 6 months. When built in, the measuring cell is accommodated in a cell housing which is so configured that only the measuring electrode is subjected to the gas to be investigated. The counter electrode is exposed to the ambient but is shielded by a diaphragm against the entry of the gas to be detected.

A reference electrode is introduced into the electrolyte in order to fix the reference potential of the measuring electrode to a specific value in the case of a so-called three-electrode cell. The reference electrode preferably is of the same composition as the measuring electrode.

BRIEF DESCRIPTION OF THE DRAWINGS

The invention will now be described with reference to the drawings wherein.

DESCRIPTION OF THE PREFERRED
EMBODIMENTS OF THE INVENTION

Figure 1:
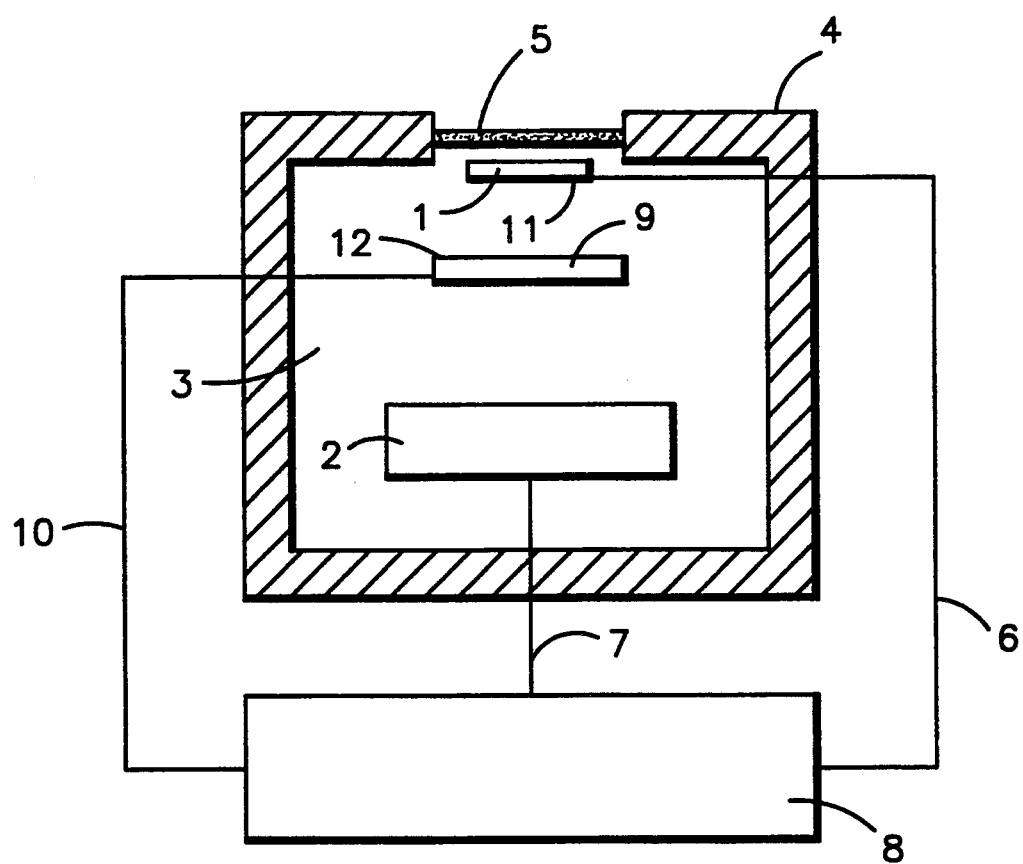
FIG. 1 is a side elevation view, in section, of a measuring cell according to an embodiment of the invention.

The electrochemical measuring cell of FIG. 1 includes an electrolyte 3 of an aqueous solution of calcium nitrate. The electrolyte is contained in a housing 4 in which a measuring electrode 1, a counter electrode 2 and a reference electrode 9 are introduced. The electrodes (1, 9) have respective coatings (11, 12) containing cobalt oxide. The electrolyte 3 is closed off in a direction facing toward the ambient containing the measuring sample by a membrane 5 which is permeable to ammonia and hydrazine and which is attached to the housing 4 in a seal-tight manner. The measuring electrode 1, the counter electrode 2 and the reference electrode 9 have respective measurement leads (6, 7, 10) which are passed through the housing 4 and connected to an evaluation device 8 for processing the measurement signals.

Figure 2:
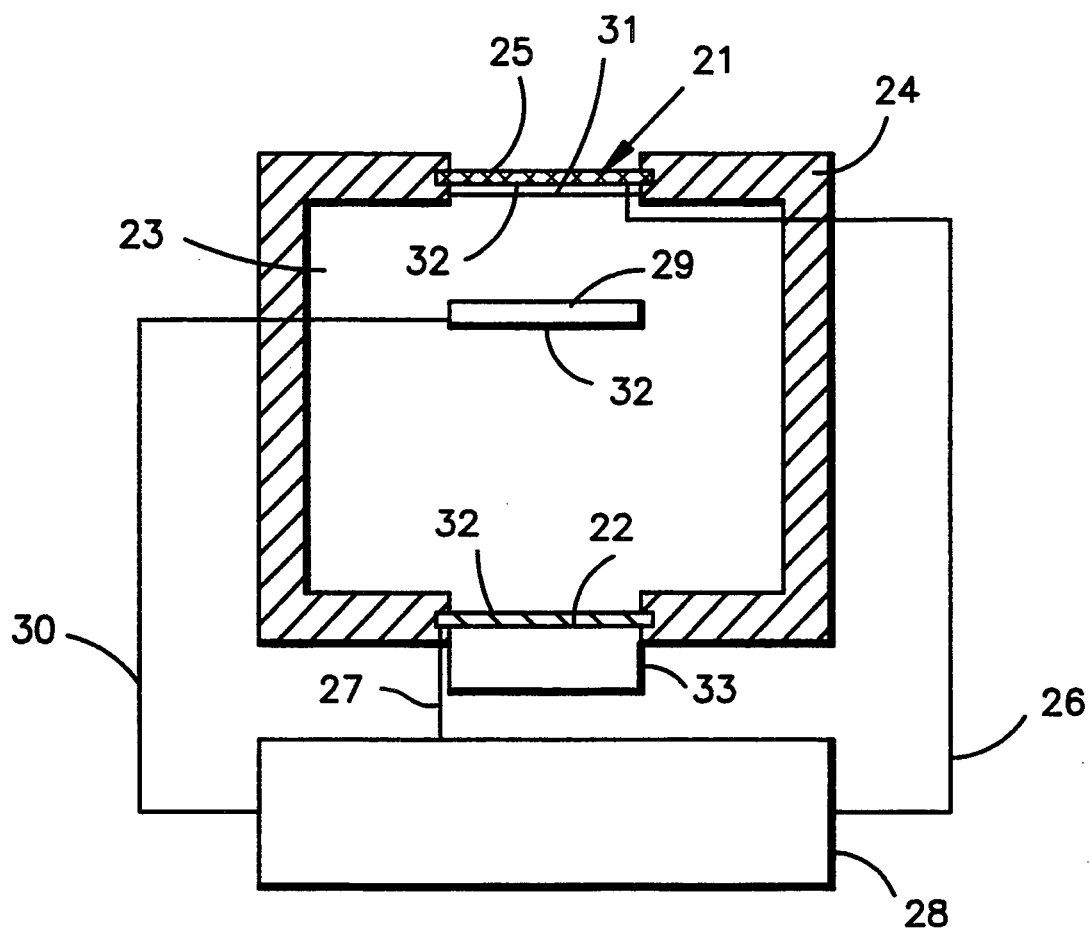
FIG. 2 is a side elevation view, in section, of a measuring cell according to another embodiment of the invention; and, FIG. 3 is a side elevation view of the filter of the measuring cell of FIG. 2.

FIG. 2 shows an electrochemical measuring cell having an electrolyte 23 of 6 Mol lithium chloride and $10^{-2}$ Mol $NH_4NO_3$ into which a measuring electrode 21, a counter electrode 22 and a reference electrode 29 are introduced. The electrodes (21, 29) comprise a carrier material of iridium applied to a PTFE-membrane 25 which is attached in the housing 24 of the measuring cell so as to be seal-tight with respect to the ambient. The membrane 25 is permeable for the ammonia, amine and hydrazine and is impermeable with respect to the electrolyte 23. The iridium coating applied to the electrolyte side of the membrane 25 is covered with a coating 32 of iridium oxide. This coating 32 is indicated schematically in FIG. 2 by a solid line periphery of the electrodes (21, 22, 29). The counter electrode 22 and the reference electrode 29 likewise comprise a carrier material made of iridium. Those surfaces of the electrodes (22, 29), which come into relationship with the electrolyte, are covered with an iridium oxide coating 32. The counter electrode 22 is part of the wall of the housing 24. A porous PTFE-membrane serves as an electrode carrier having a surface facing the ambient which is covered by a filter 33. The active surface of the measuring electrode 21 is covered with the iridium oxide coating 32 and an ion exchange membrane 31 is arranged opposite this active surface. This membrane prevents access of the hydroxide ions dissolved in the electrolyte 33 to the measuring electrode 21 even though the measuring electrode 21 is covered by the electrolyte 23. All electrodes (21, 22, 29) have respective measurement leads (26, 27, 30) which are passed through the housing 24 and are connected to an evaluation device 28 for processing the measurement signals. The evaluation device 28 furthermore includes a potentiostat with the aid of which the reference potential across the reference electrode 29 and the measuring electrode 21 is fixed and maintained.

Figure 3:
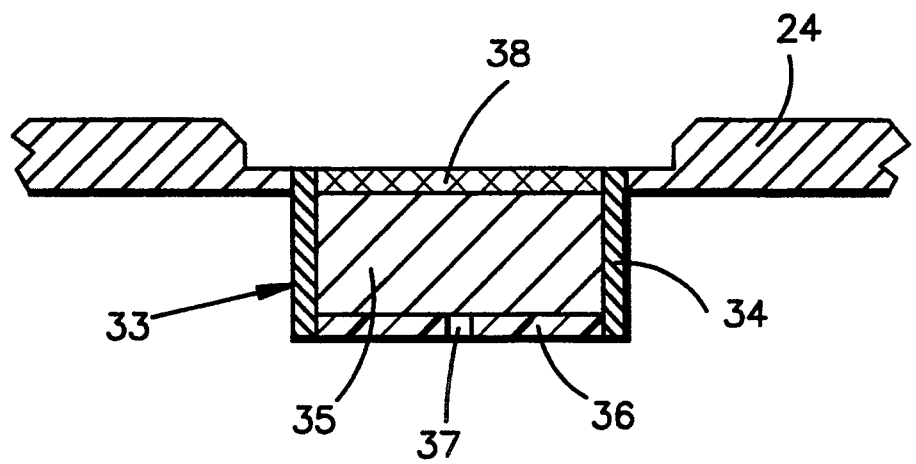

The filter 33 is shown in FIG. 3 and includes a sleeve-shaped filter housing 34. A charge 35 of activated charcoal is contained in the housing 34. The active charcoal is impregnated selectively with phosphoric acid or zinc sulfate ($ZnSO_4$). The charge 35 is closed off with respect to the ambient by a plastic disc 36 having a central bore 37 of approximately 1 mm. The housing 34 is closed by a porous polyethylene disc 38 with respect to the counter electrode 22.

It is understood that the foregoing description is that of the preferred embodiments of the invention and that various changes and modifications may be made thereto without departing from the spirit and scope of the invention as defined in the appended claims.

TABLE I

Solidification of Electrolyte Solutions at low Temperatures

| Solute | Solvent | Concentration in Mol/L | Temperature in °C. | State |
|---|---|---|---|---|
| NaCl | $H_2O$ | $10^{-4}$ to | −5 | solid |
| | | $10^{-1}$ | −5 | solid |
| KCl | $H_2O$ | $10^{-4}$ to | −5 | solid |
| | | $10^{-1}$ | −5 | solid |
| $NH_4Cl$ | $H_2O$ | $10^{-4}$ to | −5 | solid |
| | | $10^{-1}$ | −5 | solid |

TABLE II

Solidification of Electrolyte Solutions at low Temperatures

| Solute | Solvent | Concentration in Mol/L | Temperature in °C. | State |
|---|---|---|---|---|
| $LiNO_3$ | $H_2O$ | 3.5 | −10 | liquid |
| | | 3.5 | −20 | partially solid |
| LiCl | $H_2O$ | 3.5 | −25 | partially solid |
| LiCl | $H_2O$ | 6.0 | −50 | liquid |
| | | 8.0 | −50 | liquid |
| | | 10.0 | −50 | liquid |
| LiBr | $H_2O$ | 8.0 | −50 | liquid |
| | | 10.0 | −50 | liquid |
| $MgCl_2$ | $H_2O$ | 3.5 | −50 | liquid |
| $MgBr_2$ | $H_2O$ | 3.5 | −50 | liquid |
| $Ca(NO_3)_2$ | $H_2O$ | 1.0 | −30 | solid |
| | | 3.5 | −30 | solid |

What is claimed is:

1. An electrochemical measuring cell for determining ammonia or hydrazine in a fluid measuring sample present in the ambient, the measuring cell comprising:

a housing having an opening directed toward the sample to be measured and defining an electrolyte chamber;

a soluble electrolyte contained in said chamber;

a membrane mounted on said housing for closing off said chamber to the ambient and being permeable to ammonia and hydrazine;

a measuring electrode and a counter electrode disposed in said chamber so as to be in spaced relationship to each other;

said soluble electrolyte being an aqueous solution of a hygroscopic salt of an alkali metal and an ammonium salt;

said hygroscopic salt having a concentration in said aqueous solution for preventing solidification of said solution down to a temperature in the range of −10° C. to −50° C.; and, said ammonium salt having a concentration of $10^{-3}$ to $10^{-1}$ M.

2. The electrochemical measuring cell of claim 1, wherein said hygroscopic salt has a cationic component and an anionic component; said cationic component being lithium; and, said anionic component being selected from the group consisting of a nitrate, bromide and chloride; and, said ammonium salt being selected from the group consisting of ammonium nitrate and ammonium chloride.

3. The electrochemical measuring cell of claim 1, wherein said ammonium salt is an admixture of ammonium salts.

4. An electrochemical measuring cell for determining ammonia or hydrazine in a fluid measuring sample present in the ambient, the measuring cell comprising:

a housing having an opening directed toward the sample to be measured and defining an electrolyte chamber;

a soluble electrolyte contained in said chamber;

a membrane mounted on said housing for closing off said chamber to the ambient and being permeable to ammonia and hydrazine;

a measuring electrode and a counter electrode disposed in said chamber so as to be in spaced relationship to each other;

said soluble electrolyte being an aqueous solution of a hygroscopic salt of an alkaline earth metal; and, said hygroscopic salt having a concentration in said aqueous solution for preventing solidification of said solution down to a temperature in the range of −10° C. to −50° C.

5. The electrochemical measuring cell of claim 4, wherein said hygroscopic salt has a cationic component and an anionic component; said cationic component being selected from the group consisting of magnesium and calcium; and, said anionic component being selected from the group consisting of a nitrate, bromide and chloride.

6. The electrochemical measuring cell of claim 1 or 4, further comprising:
at least said measuring electrode having a coating; and,
said coating having an oxide of an element of the platinum metal group or a metal conductive oxide mixture of several elements of the platinum metal group.

7. The electrochemical measuring cell of claim 6, wherein said oxide constituent is selected from the group consisting of ruthenium dioxide, iridium dioxide and a mixture of said ruthenium dioxide and said iridium dioxide.

8. The electrochemical measuring cell of claim 6, wherein said measuring electrode is made of iridium and said coating comprises iridium dioxide.

9. The electrochemical measuring cell of claim 6, wherein said electrolyte has a neutral to acidic pH-value.

10. The electrochemical measuring cell of claim 9, said hygroscopic salt being selected from the group consisting of chloride and nitrate.

11. The electrochemical measuring cell of claim 6, said hygroscopic salt being selected from the group consisting of chloride and nitrate.

12. The electrochemical measuring cell of claim 6, further comprising an ion exchange membrane being disposed in said electrolyte between said measuring electrode and said counter electrode for preventing a hydroxide ion transport in said electrolyte.

13. The electrochemical measuring cell of claim 12, wherein said ion exchange membrane is made of perfluorosulfonated PTFE.

14. The electrochemical measuring cell of claim 12, said ion exchange membrane being a partition membrane mounted in said housing so as to extend between said measuring electrode and said counter electrode.

15. The electrochemical measuring cell of claim 12, wherein said measuring electrode has a surface, and said ion exchange membrane covers said surface of said measuring electrode.

16. The electrochemical measuring cell of claim 6, wherein said measuring electrode and said counter electrode both have the same composition.

17. The electrochemical measuring cell of claim 6, said housing having a wall and a portion of said wall being configured to include said counter electrode; said portion of said housing comprising a porous membrane impermeable to said electrolyte and having a coating formed thereon facing toward said electrolyte to serve as said counter electrode; said coating of said porous membrane defining a first surface facing toward said electrolyte and said porous membrane defining a second surface facing away from said electrolyte; and said electrochemical measuring cell further comprising a filter covering said second surface; and, said filter being adapted to accept ammonia.

18. The electrochemical measuring cell of claim 17, said filter including a housing and a charge of active charcoal contained in said housing.

19. The electrochemical measuring cell of claim 18, said charge of active charcoal being impregnated with zinc sulfate.

20. The electrochemical measuring cell of claim 18, said charge of active charcoal being impregnated with phosphoric acid.

21. The electrochemical measuring cell of claim 6, further comprising a reference electrode having the same composition as said measuring and counter electrode.

* * * * *

UNITED STATES PATENT AND TRADEMARK OFFICE
CERTIFICATE OF CORRECTION

PATENT NO. : 5,344,546

DATED : September 6, 1994

INVENTOR(S) : Herbert Kiesele, Stephan Haupt and Uwe Kühn

It is certified that error appears in the above-identified patent and that said Letters Patent is hereby corrected as shown below:

On the Title Page, in the title: delete the title and substitute -- ELECTROCHEMICAL MEASURING CELL FOR DETERMINING AMMONIA, AMINES, HYDRAZINE AND HYDRAZINE DERIVATIVES -- therefor.

In column 1: delete lines 2 to 5 and substitute -- ELECTROCHEMICAL MEASURING CELL FOR DETERMINING AMMONIA, AMINES, HYDRAZINE AND HYDRAZINE DERIVATIVES -- therefor.

In column 7, line 27: delete "solrate" and substitute -- solvate -- therefor.

UNITED STATES PATENT AND TRADEMARK OFFICE
CERTIFICATE OF CORRECTION

PATENT NO. : 5,344,546
DATED : September 6, 1994
INVENTOR(S) : Herbert Kiesele, Stephan Haupt and Uwe Kühn It is certified that error appears in the above-identified patent and that said Letters Patent is hereby corrected as shown below:

In column 7, lines 40 to 45: please delete the table and substitute therefor:

-- Working electrode:
$$2\ NH_3 = N_2 + 6\ H^+ + 6\ e^-$$
$$6\ NH_3 + 6\ H^+ = 6\ NH_4^+$$

$$8\ NH_3 = N_2 + 6\ NH_4^+ + 6\ e^-$$

Counter electrode: $O_2 + 2\ H_2O + 4\ e^- = 4\ OH^-$

Working potential: $\geq 400\ mV$ --.

Signed and Sealed this

Twenty-ninth Day of November, 1994

Attest:

*Bruce Lehman*

BRUCE LEHMAN

*Attesting Officer*     *Commissioner of Patents and Trademarks*